(12) United States Patent
Tomasi et al.

(10) Patent No.: US 6,673,806 B2
(45) Date of Patent: Jan. 6, 2004

(54) CRYSTALLINE FORM II CABERGOLINE

(75) Inventors: Attilio Tomasi, Milan (IT); Stefania Magenes, Melzo (IT); Giuliano Ramella, Vailate (IT); Mario Ungari, Milan (IT); Marco Pandolfi, Monza (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 10/239,562

(22) PCT Filed: Mar. 19, 2001

(86) PCT No.: PCT/EP01/03098

§ 371 (c)(1),
(2), (4) Date: Jan. 16, 2003

(87) PCT Pub. No.: WO01/72747

PCT Pub. Date: Oct. 4, 2001

(65) Prior Publication Data

US 2003/0187013 A1 Oct. 2, 2003

(30) Foreign Application Priority Data

Mar. 24, 2000 (GB) .............................. 0007307

(51) Int. Cl.[7] .................. A61K 31/48; C07D 457/06
(52) U.S. Cl. ......................... 514/288; 546/69
(58) Field of Search ..................... 514/288; 546/69

(56) References Cited

U.S. PATENT DOCUMENTS 4,526,892 A   7/1985  Salvati et al.

FOREIGN PATENT DOCUMENTS

GB    2 103 603    2/1983

OTHER PUBLICATIONS

P. Sabatino et al.: "X–ray crystal structure and conformational analysis of N–(3–dimethylaminopropyl)–N–ethylaminocarbonyl)–6–(2–propenyl)ergoline–8–beta–carboxamide (cabergoline)" IL Farmaco, vol. 50, No. 3, pp. 175–178 1995.

E. Brambilla et al.: "Synthesis and nidtion activity of a new class of ergoline derivative" European Journal of Medicinal Chemistry, vol. 24, pp. 421–426 1989.

*Primary Examiner*—Charanjit S. Aulakh
(74) *Attorney, Agent, or Firm*—Akin Gump Strauss Hauer & Feld LLP; Dwayne L. Mason

(57) ABSTRACT

Crystalline form II of cabergoline, a pharmaceutical composition containing it and a process for its preparation are disclosed. The process may comprise crystallization from a solution of raw cabergoline in an organic solvent at low temperatures or submitting to a slurry procedure a mixture of cabergoline Forms I and II in a solvent at a temperature below about 30° C.

10 Claims, 4 Drawing Sheets

CRYSTALLINE FORM II CABERGOLINE

This application is a 371 of PCT/EP01/03098 filed Mar. 19, 2000, now WO 01/72747.

The present invention concerns a new crystalline form of cabergoline, a pharmaceutical composition thereof and its use as therapeutically active agent, alone or in combination. Another aspect of the present invention relates to the preparation of this crystalline form.

Cabergoline is an ergoline derivative interacting with D2 dopamine receptors and is endowed with different useful pharmaceutical activities and it is used in the treatment of hyperprolactinemia, central nervous system disorders (CNS) and other related diseases.

Cabergoline is the generic name of 1((6-allylergolin-8Betayl)-carbonyl)-1-(3-dimethylaminopropyl)-3-ethylurea, described and claimed in U.S. Pat. No. 4,526,892. The synthesis of Cabergoline molecule is reported also in Eur. J. Med. Chem., 24,421, (1989) and in GB-2,103,603-B.

During our work we discovered that cabergoline can exist in at least two crystalline forms under ambient conditions. One form (coded Form I) is an anhydrous not solvated form and, to our knowledge, it is the only form reported in the literature to date. Form II is an anhydrous not solvated form too.

Thus, the present invention concerns a new polymorph (Form II) of cabergoline and the preparation thereof. Another aspect relates to samples of cabergoline Form II having a % polymorph purity >90%, preferably >99%. The invention further provides a pharmaceutical composition of cabergoline Form II and its use as therapeutic agent.

Form II is the thermodynamically most stable polymorph in a range of temperature between −70 and +30° C. It can be readily prepared starting from crude material by crystallization from several solvents at low temperatures. Alternatively it can be prepared by slurry of a mixture of forms I and II in a solvent at a temperature below 30° C. The importance of cabergoline form II rests primarily (but not exclusively) in thermodynamic stability.

Besides its greater stability, Form II shows advantages with respect to form I because of the possibility of its preparation by crystallization employing different solvents in a wide range of temperatures.

Characterisation

X-ray powder diffraction (XRD), differential scanning calorimetry (DSC), infrared (IR) spectroscopy and solid state $^{13}$C-NMR were used to characterise the new form.

X-Ray Powder Diffraction

Powder X-ray diffraction was performed using either a Scintag X1 or X2 Advanced Diffraction System operating under Scintag DMS/NT© Ver 1.30a and 1.36b respectively, and Microsoft Windows NT 4.0™ software. The system used a copper X-ray source maintained at 45 kV and 40 mA to provide CuK$\alpha_1$ emission of 1.5406 angstroms and a solid state peltier cooled detector. Beam aperture was controlled using tube divergence and anti-scatter slits of 2 and 4 mm and detector anti-scatter and receiving slits of 0.5 and 0.3 mm width. Data were collected from 2 to 400 two-theta using a step scan of 0.03°/point with a one second/point counting time. The samples were hand ground using a pestle and mortar and packed into an aluminum sample tray with a 12 mm (diam.)×0.5 mm cavity.

DSC

Measurements of differential scanning calorimetry were obtained on a Mettler TA 4000 thermal analysis system. Approximately 8.5 mg samples were accurately weighed into a DSC pan. The pans were hermetically sealed and a pinhole was punched into the pan lid. The use of the pinhole allows for pressure release, but still assures that the thermal reactions proceed under controlled conditions. The samples were introduced into the DSC oven and then heated at a rate of 5 DEG C./min, up to a final temperature of 135 DEG C.

IR Spectroscopy

IR spectrum of cabergoline form II was obtained on a Perkin Elmer FT-IR spectrophotometer PARAGON 1000. The sample was prepared by KBr powder technique registering the spectrum on reflectance.

Solid state $^{13}$C-NMR

Solid state $^{13}$C-NMR spectra were obtained on a MSL 300 Bruker instrument equipped with solid state facilities and variable temperature magic angle spinning probe. Cross polarization experiments were performed by a decoupling field of 50 KHz and single pulse magic angle spinning experiments with recycle times ranging from 10 to 100 records.

The XRD, DSC, IR and NMR curves are shown in FIGS. 1–4 respectively.

The x-ray powder diffraction pattern for Form II (FIG. 1) shows a crystalline structure with useful distinctive peaks at approximately 8.5, 9.4, 11.6, 16.5 and 21.5 deg 2-theta.

Figure 1:
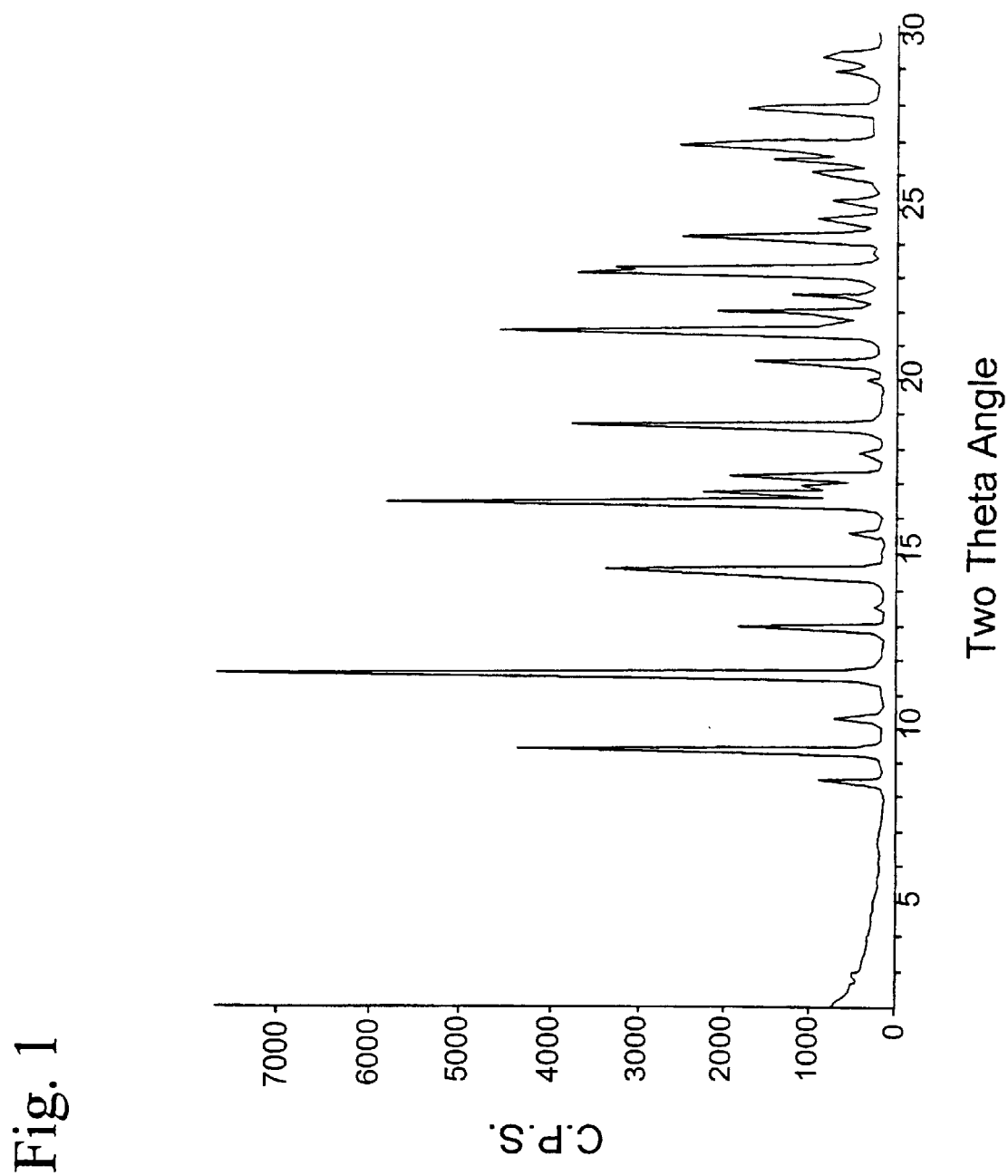
FIG. 1. XRD powder pattern of cabergoline Form II.
Figure 2:
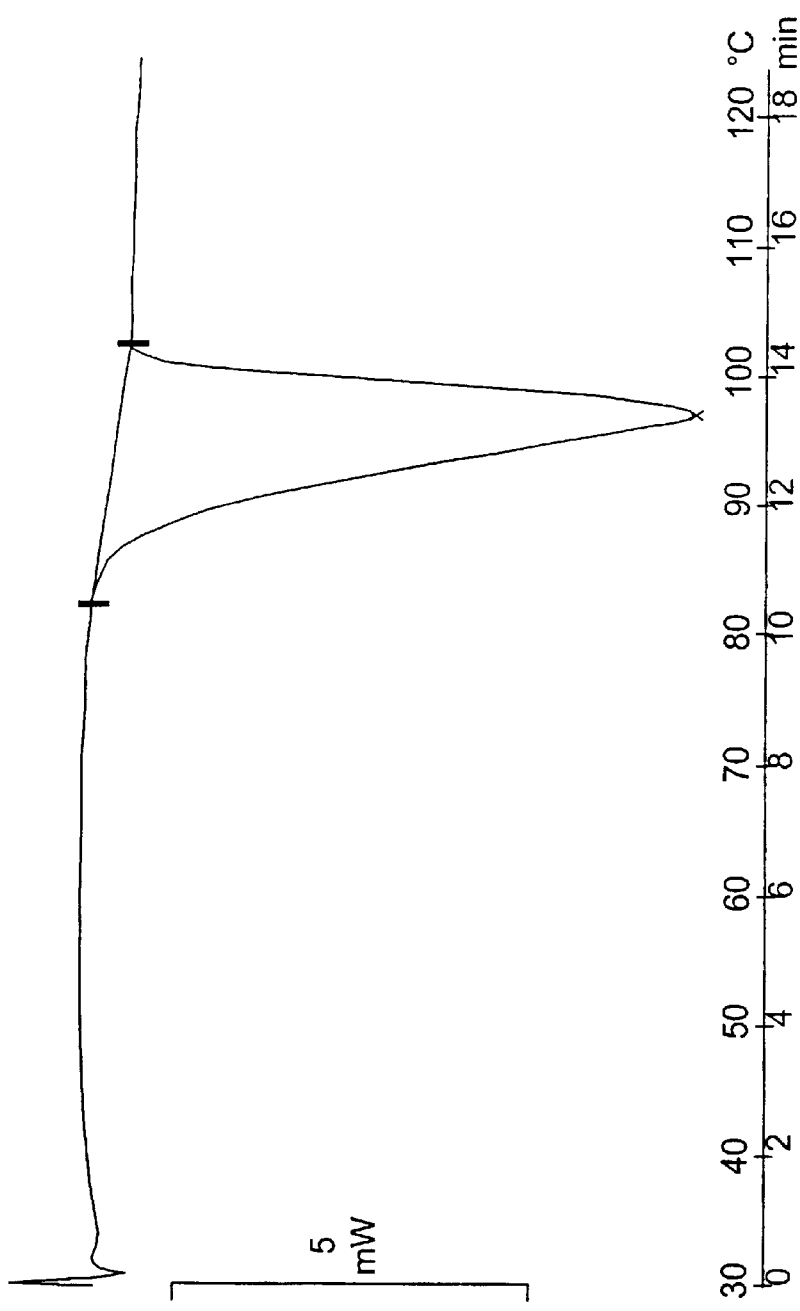
FIG. 2. DSC curve of cabergoline Form II.
Figure 3:
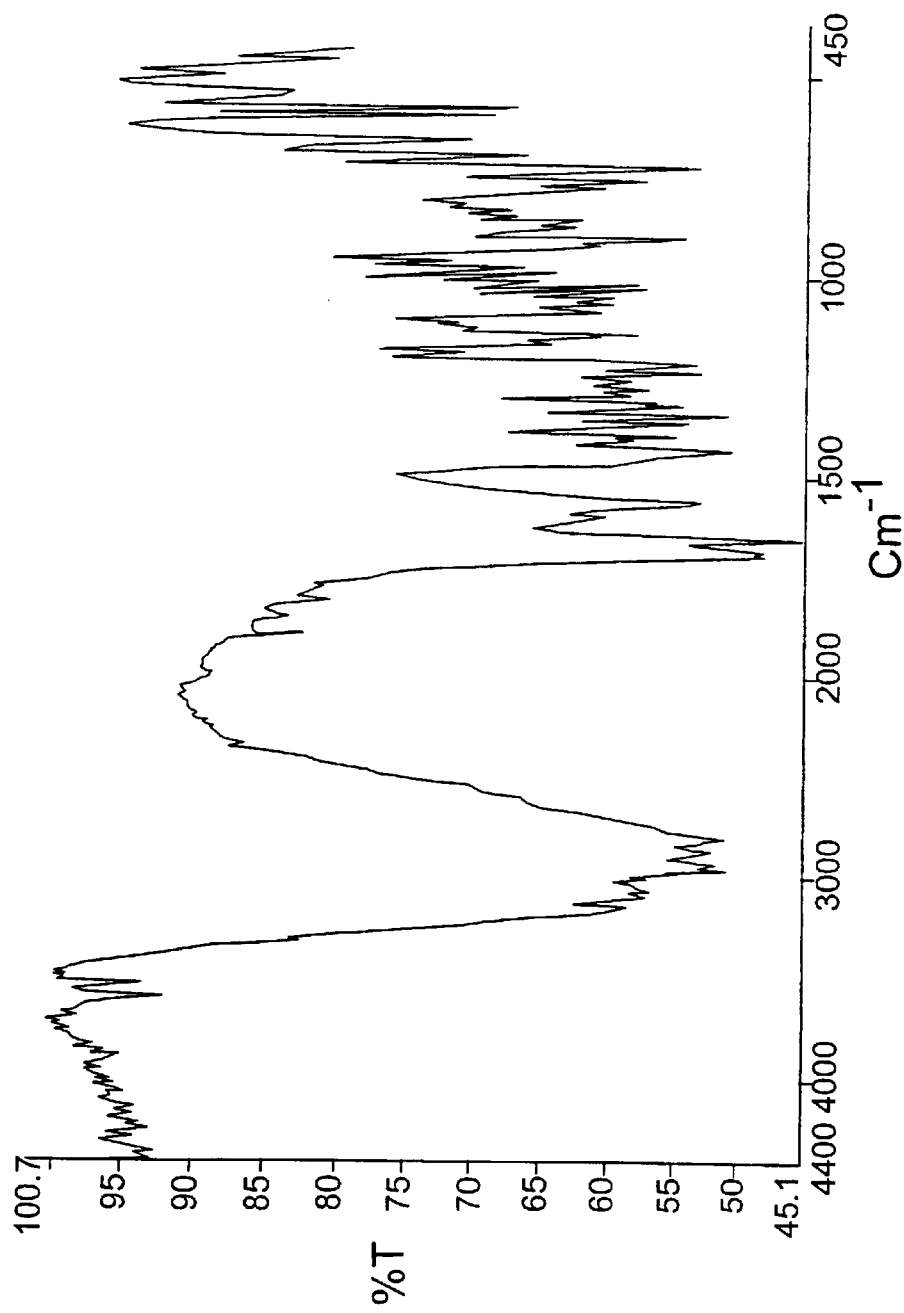
FIG. 3. IR spectrum of cabergoline Form II (sample prepared by KBr powder technique).

The DSC curve of Form II (FIG. 2) exhibits a melting endotherm at approximately 96–102° C. The integrated melting endotherm has a heat of fusion of approximately 7C J/g. The IR spectrum of Form II is shown in FIG. 3. It shows a characteristic double band at about 1670 and 1690 cm$^{-1}$ due to carbonyl stretching.

Figure 4:
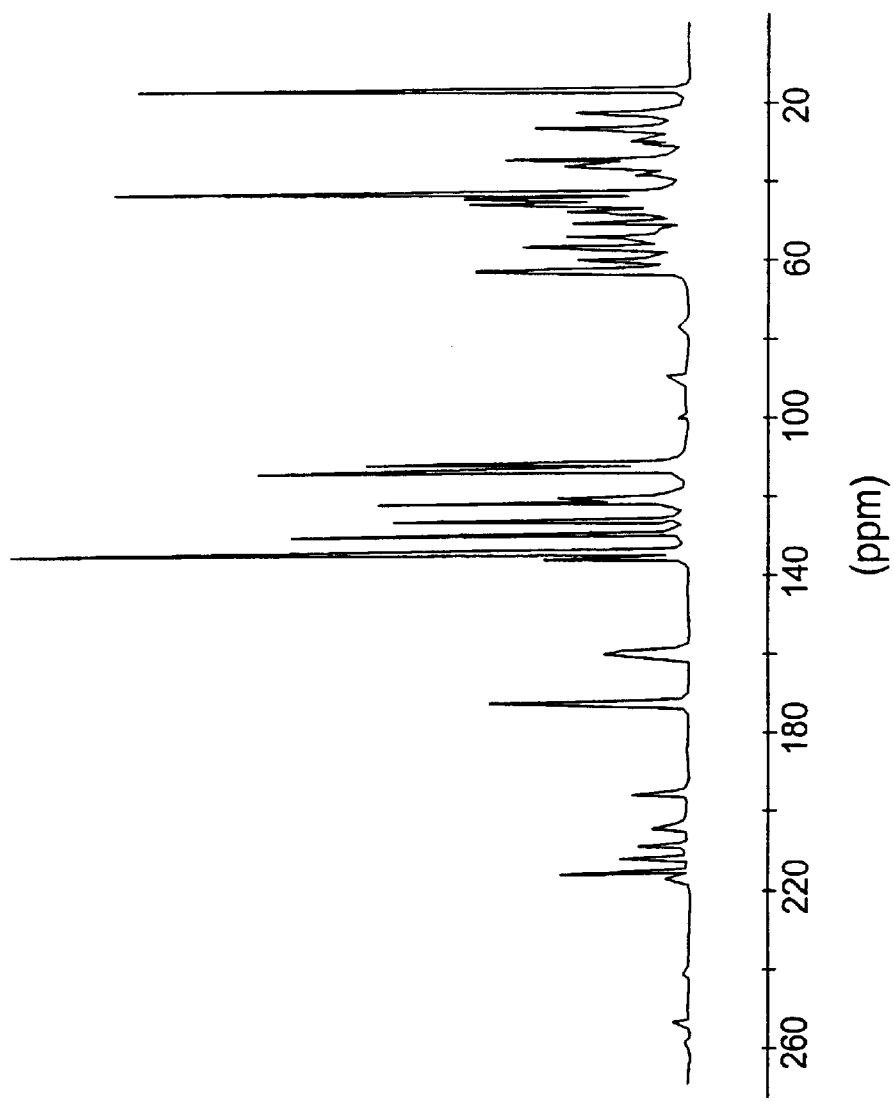
FIG. 4. Solid state $^{13}$C-NMR spectrum of cabergoline form II.

The solid state $^{13}$C-NMR spectrum of form II is shown in FIG. 4.

These data indicate that cabergoline Form II is a crystalline polymorph easily distinguishable from form I by XRD, IR and solid state $^{13}$C-NMR techniques. Also DSC, when combined with another analytical technique, is a method to distinguish the two polymorph forms.

Crystalline cabergoline I has been reported in Il Farmaco, 50 (3), 175–178 (1995). However, to applicants' knowledge, no one has reported any other crystalline form. In summary, cabergoline exists in at least two crystalline forms. Form I is a crystal (melting point=98–105° C. by DSC, heat of fusion of ~60 J/g) with a characteristic powder XRD pattern and an IR spectrum very different from that of form II.

Form II is a crystal (melting point=96–102° C. by DSC, heat of fusion about 70 J/g) with characteristic powder XRD pattern and IR spectrum.

The present invention also provides a process for producing Form II solids by crystallisation from an organic solvent or from a mixture of organic solvents. The process comprises dissolving the raw final cabergoline, obtained as an oil through the synthesis described in Eur. J. Med. Chem.,24, 421, (1989), in a suitable amount of an organic solvent. Suitable organic solvents include ketones, acetals, ether, esters, and the mixture thereof. Ketones and esters include straight or branched $C_3$–$C_6$ ketones, $C_2$–$C_4$ esters such as acetone, methyl ethyl ketone, methyl acetate.

Ether solvents include straight or branched $C_4$–$C_5$ ethers such as diethyl ether, methyl t-butyl ether. Preferred solvents are diethyl ether, methyl acetate, diethoxymethane (ethylal), methyl tert-butyl ether, acetone or methyl ethyl ketone. The resultant solution is then concentrated and cooled. Preferably the solution is kept at about −5° C. for 1 to 7 days, preferably for 1–3 days. The thus obtained crystals may be recovered by common procedures, for example by filtration under reduced pressure of by centrifugal filtration, followed by drying the crystals, to obtain the crystalline Form II cabergoline of the present invention. Crystalline Form II cabergoline may be also prepared by subjecting a mixture of crystal forms I and II of cabergoline to a slurry procedure at a temperature below 30° C.

Preferably, the mixture is stirred at room temperature in organic aliphatic linear $C_{4-7}$ alkanes or $C_4$–$C_5$ ethers such as n-hexane or diethyl ether. In the mixture, the Form I/Form II ratio is preferably from 10:1 to 1:10. The resultant crystals were collected as above described.

Like cabergoline Form I, Forms II displays a significant inhibitory effect with regard prolactine and has therapeutic properties that make it possible to treat patients who have pathological conditions associated with an abnormal prolactin level, thus is useful in human and/or veterinary medicine. Cabergoline is also active, alone or in combination, in the treatment of reversible obstructive airways diseases, for controlling intraocular pressure and for the treament of glaucoma. It is also employed in the veterinary field, as antiprolactin agent and in cutting down drastically the proliferation of vertebrate animals. The several uses of cabergoline are for example described in WO9948484, WO9936095, U.S. Pat. No. 5705510, WO9505176, EP040325. Forms II in accordance with the invention is particularly useful in the treatment of Parkinson's disease (PD), Restless Legs Syndrome (RLS), treatment of diseases like Progressive Supranuclear Palsy (PSP) and Multysystemic atrophy (MSA). Thus, another aspect of the instant invention concerns a method for treatment of Parkinson's disease (PD), Restless Legs Syndrome (RLS), Progressive Supranuclear Palsy (PSP) and Multysystemic atrophy (MSA) which comprises administering to a host an effective amount of cabergoline Form II.

Cabergoline Forms II of the present invention may be used in a manner similar to that of cabergoline Form I; therefore, a person skilled in the art of CNS diseases treatment will be able to ascertain, without undue experimentation, an appropriate treatment protocol for administering a compound of the present invention. The dosage, mode and schedule of administration for compounds of this invention are not particularly restricted, and will vary with the particular compound employed. Thus Forms II of the present invention may be administered via any suitable route of administration, preferably orally. For CNS diseases treatment, the dosage may be, for example, in the range of about 0.5 to about 50 mg/patient/day, preferably 2 to 4 mg daily as monotherapy and 2 to 6 mg daily as adjuvant therapy. The actual dose used will vary according to the particular composition formulated, the route of administration, and the particular disease being treated. Many factors that modify the action of the drug will be taken into account in determining the dosage including age, weight, sex, diet and the physical condition of the patient.

The present invention also provides pharmaceutical compositions (formulations) containing an effective amount of Form II in combination with one or more pharmaceutically acceptable carriers, excipients, diluents or adjuvants. For example, Form II invention may be formulated in the form of tablets, pills, powder mixtures, capsules, injectables, solutions, suspensions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration as a suspension (microdispersion) or in solution.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

EXAMPLE 1

The oil obtained by purification on a chromatographic column after the final step of the synthetic path according to the preparation described in Eur. J. Med. Chem.,24, 421, (1989) and containing 37 g of pure cabergoline was dissolved in 600 ml of diethyl ether. 1.8 g of carbon and 18 g of sodium sulphate were added, and the mixture was stirred for one hour at room temperature and then filtered on a GF/F filter under vacuum. The filter was washed with 50 ml of diethyl ether and the collected solution, concentrated until a volume of about 80 ml, was transferred into a reactor and cooled at −5° C. for 1–4 days. The suspension was filtered using a glass filter under vacuum and the crystalline solid cake was washed with 50 ml of diethyl ether pre-cooled at −5° C. The resulting crystals were then dried under vacuum at 35° C. until constant weight. Yield was about 70% on the basis of pure cabergoline initial content. The resultant crystal Form II, having a polymorphic purity >98%, was identified by XRD, DSC, IR and NMR, data shown in FIGS. 1–4 respectively.

EXAMPLE 2

The oil containing 35 g of pure cabergoline was dissolved in 210 ml of methyl acetate. 1.8 g of carbon and 18 g of sodium sulphate were added, and the mixture was stirred for one hour at room temperature and then filtered on a GF/F filter under vacuum. The filter was washed with 50 ml of methyl acetate, and the collected solution, concentrated until a volume of about 80 ml, was transferred into a reactor and cooled at −10° C. for 1–3 days. The suspension was filtered using a glass filter under vacuum and the crystalline solid cake was washed with 50 ml of methyl acetate pre-cooled at −10° C. The crystals were then dried under vacuum at 35° C. until constant weight, yield about 70%. The analytical data were the same of example 1.

EXAMPLE 3

The oil containing 38.6 g of pure cabergoline was dissolved in 850 ml of ethylal. 1.8 g of carbon and 18 g of sodium sulphate were added, and the mixture was stirred for one hour at room temperature and then filtered on a GF/F filter under vacuum. The filter was washed with 50 ml of ethylal, the collected solution, concentrated until a volume of about 100 ml, was transferred into a reactor and cooled at −5° C. for 1–4 days. The suspension was filtered using a glass filter under vacuum and the crystalline solid cake was washed with 50 ml of ethylal pre-cooled at −5° C. The crystals are then dried under vacuum at 35° C. until constant weight, yield about 50%. The analytical data were the same of example 1.

EXAMPLE 4

The oil containing 30.5 g of pure cabergoline was dissolved in 650 ml of methyl tert-butyl ether. 1.8 g of carbon and 18 g of sodium sulphate were added, and the mixture stirred for one hour at room temperature and then filtered on a GF/F filter under vacuum. The filter was washed with 50 ml of methyl tert-butyl ether. The collected solution, concentrated until a volume of about 100 ml, was transferred into a reactor and cooled at −5° C. for 1–2 days. The suspension was filtered using a glass filter under vacuum and the crystalline solid cake was washed with 50 ml of methyl tert-butyl ether pre-cooled at −5° C. The crystals formed, probably a solvated form, were dried under vacuum at 35° C to give form II, yield about 75%. The analytical data were the same of example 1.

EXAMPLE 5

A mixture of 200 mg of form I and of an equal amount of form II was added to 50 ml of n-hexane at 25° C. The suspension was stirred for about 12 hours, then filtered using a glass filter under vacuum. The collected crystals were identified by analytical methods as pure form II. The analytical data were the same of example 1.

EXAMPLE 6

A mixture of 50 mg of form I and of 350 mg of form II was added to 5 ml of diethyl ether at −5° C. The suspension was stirred for about 12 hours, then filtered using a glass filter under vacuum. The collected crystals were identified by analytical methods as pure form II. The analytical data were the same of example 1.

What is claimed is:

1. Crystalline form II of cabergoline.
2. Crystalline form II of cabergoline according to claim 1 which is anhydrous, non-solvated and has a percentage purity greater than 85%.
3. Crystalline form II of cabergoline according to claim 1 which is anhydrous, non-solvated and has a percentage purity greater than 98%.
4. Crystalline form II of cabergoline having the XRD powder pattern of FIG. 1.
5. A pharmaceutical composition which comprises an effective amount of crystalline Form II as defined in claim 1, in combination with one or more pharmaceutically acceptable carriers, excipients, diluents or adjuvants.
6. A process for producing cabergoline Form II as defined in claim 1, which process comprises crystallisation of the desired form II from a solution of raw cabergoline in an organic solvent at a low temperature.
7. A process according to claim 6 in which the organic solvent is a ketone, an acetal, a linear ether, an ester or mixture thereof.
8. A process according to claim 6 in which the solvent is diethyl ether or methyl tert-butyl ether.
9. A process for producing cabergoline Form II as defined in claim 1, which process comprises subjecting a mixture of cabergoline forms I and II in a solvent at a temperature below about 30° C. to a slurry procedure.
10. A process according to claim 9 in which the solvent is diethyl ether or n-hexane.

* * * * *